United States Patent [19]

Squirrell

[11] Patent Number: 5,648,232
[45] Date of Patent: Jul. 15, 1997

[54] MICROBIOLOGICAL BEST METHOD AND REAGENTS

[75] Inventor: David James Squirrell, Wiltshire, United Kingdom

[73] Assignee: The Secretary of State for Defence in her Britannic Majesty's Government of the United Kingdom of Great Britain and Northern Ireland, England

[21] Appl. No.: 634,222

[22] Filed: Apr. 18, 1996

Related U.S. Application Data

[63] Continuation of Ser. No. 407,889, Mar. 21, 1995, abandoned.

[30] Foreign Application Priority Data

Jan. 21, 1993 [GB] United Kingdom ............... 9301118

[51] Int. Cl.$^6$ ............................ C12Q 1/02; C12Q 1/66; C12Q 1/48
[52] U.S. Cl. ..................... 435/34; 435/29; 435/4; 435/8; 435/15; 435/283.1; 435/288.1; 435/288.3; 422/68.1
[58] Field of Search ........................ 435/34, 29, 4, 435/8, 15, 283.1; 422/68.1, 288.1, 288.3

[56] References Cited

U.S. PATENT DOCUMENTS 3,933,592  1/1976  Clendenning ................. 425/29
4,303,752  12/1981  Kolehmainen et al. ......... 435/29
5,004,684  4/1991  Simpson et al. .............. 435/8

FOREIGN PATENT DOCUMENTS 0 054 676  6/1982  European Pat. Off. .
0 238 352  9/1987  European Pat. Off. .
9400118    1/1994  United Kingdom .
9417202    8/1994  WIPO .

OTHER PUBLICATIONS

Kahru et al, "Microbios", vol. 62, pp 83-92, 1990.

J. Of Biochemical and Biophysical Methods 1 (1979) 163-169 Brolin et al "Photokinetic Microassay of Adenylate Kinase Using the Firefly Luciferase Reaction".

Chemical Abstracts vol. 96, 1982 p. 350 177160k "Determination of adenosine nucleotides . . . ".

*Primary Examiner*—John Kight
*Assistant Examiner*—Louise Leary
*Attorney, Agent, or Firm*—Nixon & Vanderhye

[57] ABSTRACT

A method for detecting the presence and/or mount of microorganisms is described by adding adenosine diphosphate (ADP) to a sample suspected of containing microorganisms and/or their intracellular material, determining the amount of adenosine triphosphate (ATP) generated by adenylate kinase present, for example using a bioluminescent assay involving luciferase and luciferin, and relating the results to the presence and/or amount of microorganism. Test kits and apparatus for use in the method are also described.

45 Claims, 3 Drawing Sheets

- ● FRESH, UNWASHED CELLS
- □ FRESH, WASHED CELLS
- ▼ CELLS STORED 3 DAYS AT 37°C, UNWASHED
- ▽ SPENT MEDIUM FROM FRESH CELLS

MICROBIOLOGICAL BEST METHOD AND REAGENTS

This is a continuation of application Ser. No. 008/407,889, filed Mar. 21, 1995, now abandoned.

FIELD OF THE INVENTION

The present invention relates to a method for detecting microorganisms, to apparatus for carrying out the method and to test kits comprising essential reagents for carrying out the method.

BACKGROUND OF THE INVENTION

All living organisms utilise adenosine triphosphate (ATP) as a source of chemical energy and it is known to assay this using the ATP driven luciferase/luciferin reaction. Light generated by this enzymic reaction can be measured using a luminometer and related to the amount of ATP present. The usefulness of ATP as an index of microbial numbers has been known since the mid 1960's (see ATP Luminescence Rapid Methods in Microbiology (1989) editor Stanley et al.; Blackwell Scientific Publications, London, see pages 1–10); its main advantage being speed and sensitivity. Utilising this assay format simple samples can be analysed in a matter of minutes while complex ones routinely take only half an hour with a detection capability provided down to $10^{-12}$ mol/l ATP. There is however a need for methods which provide still further sensitivity when detecting microorganisms or their contents while retaining speed and ease of performance.

The present inventor has now determined that the speed and sensitivity of the ATP based method can be enhanced significantly by shifting the target of the assay from ATP to the enzyme which generates it, adenylate kinase. Adenylate kinase is an enzyme used by all organisms for the conversion of adenosine diphosphate (ADP) and phosphate to adenosine triphosphate (ATP). The targeting of this enzyme in preference to ATP, by using the preferred method, apparatus and kits of the invention, allows the detection of down to at least $10^{-20}$ moles of intracellular marker adenylate kinase.

It is known to assay adenylate kinase using the luciferase/luciferin system (see Brolin et al Journal of Biochemical and Biophysical Methods 1 (1979) 163–169) for the purpose of determining its activity in certain mammalian and plant tissues (Rodionova et al Fiziologiya Rastenii (1978) 25, 4, p731–734 for plants). The use of such assay system for the detection of microorganisms however has not been suggested and the advantages of doing such, ie. enhanced sensitivity so provided, have not been relevant to those studying the enzyme itself.

Although adenylate kinase is present in smaller quantities than ADP or ATP, its use as a biological marker for microorganisms provides enhanced sensitivity with a typical amplification available of 400,000 by measuring its presence through the ATP it produces; that is for every mole of enzyme present 400,000 moles of ADP are converted to ATP in a 10 minute incubation. Thus estimation of the enzyme by measuring the substrate or product of the reaction it catalyses provides for detection down to as low as $10^{-20}$ moles.

BRIEF DESCRIPTION OF THE INVENTION

A first aspect of the present invention provides a method for determining the presence and/or amount of microorganisms and/or their intracellular material present in a sample comprising estimating the amount of adenylate kinase therein by its ability to convert adenosine diphosphate (ADP) to adenosine triphosphate and relating that to the presence and/or amount of microorganisms and/of their intracellular material. This conversion is enabled by adding ADP to samples.

Adenosine triphosphate (ATP) is preferably detected by use of the luciferin/luciferase system to provide a photometrically detectable signal indicative of the amount of ATP in the sample. Luciferin/luciferase preparations and methods for their use in assaying ATP will be well known to those skilled in the art and are commercially available (eg. see Brolin et al). A typical formulation contains eg. 0.1 to 10 mg/litre luciferase, 15 to 1000 μmol/litre D-luciferin, and agents such as $MgCl_2$, EDTA, BSA, and pH 7 buffer (see eg. EP 054676).

It will be realised by those skilled in that art that the conversion of ADP to ATP requires the presence of magnesium ions. As all cells contain these ions to some degree the method of the invention does not essentially require their addition, but clearly their addition would optimise conversion rates and normalise reaction conditions such that samples deficient in magnesium can be assayed for adenylate kinase to give a signal comparable with samples replete in magnesium ions. The present inventor has accordingly found that such addition increases the sensitivity and reliability of the assay.

Thus in a preferred method of the first aspect of the present invention there is provided a method for determining the presence and/or amount of microorganisms and/of their intracellular material present in a sample characterised in that the amount of adenylate kinase in the sample is estimated by mixing the sample with adenosine diphosphate (ADP), determining the amount of adenosine triphosphate (ATP) produced by the sample from this ADP, and relating the amount of ATP so produced to the presence/or amount of adenylate kinase and to microorganisms and/or their intracellular material, wherein the conversion of ADP to ATP is carried out in the presence of magnesium ions at a molar concentration sufficient to allow maximal conversion of ADP to ATP.

The amount of magnesium present is preferably such that there is sufficient to provide one mole of magnesium for one mole of ADP such that all of the ADP molecules may be associated with at least one magnesium ion.

In preferred embodiments of this aspect of the invention the sample is provided in the form of an aqueous suspension or solution and the estimation of adenylate kinase, and thus microorganisms and/or intracellular material in the sample, is carried out by adding ADP and magnesium ions to the sample under conditions whereby any adenylate kinase present will convert ADP to ATP, incubating the sample for a predetermined period to effect such conversion, adding luciferase and luciferin agents, determining the amount of light emitted from the sample and relating that to presence and amount of adenylate kinase.

As with any amplifying assay, the sensitivity of the adenylate kinase assay of the present invention is limited by the purity of the reagents. In this case the significant contaminants are ATP in the ADP substrate and adenylate kinase in the luciferase preparation. For use as a sensitive assay for microorganisms, particularly where these may be potentially harmful and need detecting in low numbers, it is necessary that the purity of each of the reagents be as high as possible with respect to the substance which is to be assayed and with which it is to react in the assay.

To address the first problem, high purity commercial ADP (>99.5% purity) is preferably used after further purification by column chromatography. This is desirable because even small amounts of contaminating ATP may be sufficient to cause a high background reading. For example, using a diethylaminoethylcellulose column and 0.02 mM hydrochloric acid eluent, ATP is eluted more slowly from the column than ADP to a degree enabling substantial separation. Other chromatographic methods, media and eluent combinations may also be used to similar effect; eg. HPLC using Nucleosil column packings (available from Technicol, Stockport Cheshire UK), such as Nucleosil 3 and Nucleosil 5, using 0.06M $KH_2PO_4$:methanol in 77:23 ratio v/v at pH 6 with 5 mM tetrabutylammonium hydrogen sulphate. Fractions with high ADP to ATP ratios are retained for use and purity is assessed by luciferin/luciferase reagent mediated bioluminescence after adenylate kinase action to measure ADP levels and without adenylate kinase to measure ATP contaminant levels.

Using a preferred Econopaq Q strong anion exchange gel cartridge (Biorad) equilibrated with 20 mM potassium phosphate at pH 4.6 and eluting with steps of $KP_i$ concentration up to 400 mM, ADP was found to be strongly retained and eluted as a coherent peak, with ATP eluting after it. In this manner ADP with a molar % ATP upper limit of $2\times10^{-8}$ was obtainable. The most pure ADP the applicants are aware of from the literature is 0.001% (see Shutenko etal, as above) thus the present invention now provides ADP for use in the method of the present invention that has less than 0.001 molar % ATP, more preferably $2\times10^{-8}$ molar % or less; levels previously unreported.

A further method for removing ATP from the ADP substrate uses enzymes that specifically degrade ATP, such as luciferase or apyrase. Such enzymes may also be used to further purify chromatographically purified ADP, or alternatively enzymically purified ADP may be treated by column chromatography. It will be noted that apyrase is also an ADPase, but as some apyrases are more active on ATP and ADP is present at much higher levels this does not present a significant problem.

Optimum ADP concentration lies between 0.005 mM and 1 mM while changing $Mg^{2+}$ concentration in the range 10 to 30 mM has little effect. The amount of ADP with which the sample is mixed is preferably sufficient to provide an ADP concentration in the mixture in excess of 0.005 mM, more preferably in excess of 0.01 mM and most preferably in excess of 0.08 mM. A particularly preferred amount of ADP in the conversion step mixture is about 0.1 mM. Upper practical limits for ADP and $Mg^{2+}$ will be readily determined by bench experimentation without undue burden or inventive requirement by assay of know amounts of bacteria.

Where reagents are to be used which contain magnesium ion depleting agents, eg. chelating/sequestering agents such as EDTA and phosphate buffers, it will be realised that in order to provide the ADP with sufficient magnesium ions for it to undergo optimal conversion that it will be preferred for an excess of magnesium ions to be present. For the preferred concentrations of ADP set out above, the preferred concentration of magnesium ions in the suspension or solution during conversion of ADP to ATP is 1 mM or more, more preferably 5 mM or more and most preferably 10 mM or more. The magnesium ions may be provided in the form of any magnesium salt, preferably as magnesium acetate.

Further preferred formats of the method of the invention add luminometry reagents, e.g. Luciferase/luciferin, to the sample at the beginning of the incubation, preferably as a single reagent with the ADP and magnesium ion source. Luciferase is preferably stored separately from extractant.

In formats of the invention where all the reagents are included at the start of the conversion of ADP to ATP in this manner, and/or where luminometer counting is continued after luciferin/luciferase addition where that is a separate step, magnesium may be provided by the luciferin/luciferase reagent. However, due to binding of magnesium ions by EDTA and phosphate it is necessary that the amount of magnesium ions is positively ensured by prior experiment or calculation. It will be realised by those skilled in the art that the optimal amount of magnesium salt to be added to a given ADP, sample and luciferin/luciferase mixture will be readily determinable by routine experiment using a sample containing a known amount of bacteria, eg. *E. coli.* whereby maximal signals are obtained. FIG. 3 below gives an indication of the optimal amount of magnesium acetate to be added to a mixture as used in the Examples below.

As $Mg^{2+}$ ions facilitate ADP depletion by contaminant adenylate kinase, it is preferred not to keep them in solution together prior to use; chelating agent such as EDTA may be included in the ADP to prevent this. Preferably the magnesium and ADP are brought together just prior to use or in the ADP conversion step. Where the reagents are to be kept together it is preferred that they are kept in freeze dried form to avoid any premature ADP conversion to ATP.

In preferred methods of this aspect of the present method of the invention the reagents used are treated to remove adenylate kinase to high degrees of purity whereby the number of microorganisms that can be detected is of the order of tens rather than hundreds per 200 µl sample, and readings with linear relation between cells and ATP derived light are possible down to 10 cells or still lower.

Adenylate kinase, as an essential "housekeeping" enzyme, is present in virtually all cellular organisms and is generally present in luciferase preparations. It may only be a minor contaminant, but since the aim is to measure very low adenylate kinase levels in samples, its presence in the luciferase may be a limiting factor by causing high background readings. In fact the applicant has determined that, defining one unit (U) of activity as the amount of enzyme which converts 1 µmol ADP to 1 µmol ATP per minute in the presence of 0.5 mM ADP and 4.5 mM $Mg^{2+}$ at pH 7.8 at 20° C., commercial luciferases may contain $10^{-7}$U/ml or more adenylate kinase activity whereas luciferin, its substrate, comprises very little, if any, activity.

Furthermore it is common to stabilise luciferase reagents with a stabiliser, commonly a protein such as bovine serum albumin (BSA), and commercial preparations of this have been determined by the applicant to possess significant adenylate kinase activity.

The molecular weights of luciferase and adenylate kinase are significantly different, being 61 kD and 21 kD respectively. Furthermore luciferase is a membrane bound protein and therefore relatively hydrophobic, whereas adenylate kinase occurs as a soluble enzyme. It is thus possible to remove adenylate kinase from luciferase preparations by, eg. size exclusion chromatography, reverse phase chromatography, or both. Alternatively or in addition to this, the problem of adenylate kinase contamination of luciferase can be avoided by adding the bioluminescent reagents (luciferase and luciferin) just before or as measurements are taken so that any contaminating adenylate kinase does not have the time to produce a significant effect.

Suitable methods for purifying luciferase use column chromatography fractionation with a low porosity gel, e.g. Sephadex G-25 (see Nielsen and Rasmussen, Acta Chemica Scandinavica 22 (1968) p1757–1762); use of Sephadex and Sepharose columns (e.g. Blue Sepharose) in series and/or SDS electrophoresis (see Devine et al, Biochimica et Biophysica Acta 1172 (1993) 121–132); or ageing for a period at elevated ambient temperature.

In order to remove adenylate kinase activity from agents such as bovine serum albumin it is similarly possible to use column chromatography. A further treatment that has proved successful in this regard is chemical treatment of the BSA such that its ability to stabilise the luciferase is retained, but adenylate kinase activity is reduced or depleted altogether. Any conventional chemical treatment for the depletion of enzymic activity from proteins may equally be applied for this purpose. Alternatively a non-protein luciferase stabiliser, eg. glycerol, may be used as a supplement or replacement for the BSA.

For example, the applicant has determined that commercially available BSA can have its adenylate kinase activity reduced to less than 2% of its original activity or less merely by heat treatment at acid or alkaline pH. One suitably effective treatment heats the BSA at pH 5.6 or pH 10 at 50° C. for 24 hours. A further source of adenylate kinase free BSA is the chemically treated reagent acetylated-BSA, available from Sigma and BDH. It will be realised by those skilled in the art that other chemically treated BSAs will also be suitable.

In order to render all the adenyl kinase associated with a target microorganism available to the ADP and luciferase/luciferin assay reagents of the present invention it will be necessary to disrupt them such that intracellular material is released or otherwise exposed to the reagents. Such disruption might be carried out using mechanical means such as an ultrasonic generator, by use of osmotic shock optionally in association with cold shock or such agents as lysozyme or, more conveniently, by use of detergents.

Such detergents are commercially available and commonly referred to as 'extractants'. Typical extractants include generic cationic detergents such as CTAB (cetyl trimethyl ammonium bromide), and proprietory agents such as Enzymatics ATP releasing agent, Biotrace XM extractant (available from Biotrace, Bridgend UK), and Lumac NRM (nucleotide releasing agent available from Lumac BV, Holland). When using CTAB a convenient preparation will include 0.01 to 1% CTAB in water. eg 0.2%, but other concentrations may occur to those skilled in the art.

Thus before adding ADP and luciferase/luciferin reagent (s) to an assay sample suspected of containing microorganisms it is preferred to disrupt these to render their intracellular contents accessible to luminometry reagents by use of disrupting agent. If it is desired to distinguish between target cells and other cells eg. eucaryotic cells such as those of fungal spores it is possible to run two separate assays treating one with nonionic detergent capable of disrupting only these spores and eucaryotic cells such as multi-cellular 'somatic' animal cells (eg. Triton TX-100), and the other with cationic detergent 'extractants' detailed above for disrupting all cells. It is possible to carry out these assays on the same sample if an ATPase such as apyrase is added between detergent/luciferase/measurement cycles; one cycle using nonionic and the other cationic detergent in a first cycle step with filtration steps between them.

As stated above, although other assays may be used, ATP is preferably detected by use of the luciferin/luciferase system to provide a photometrically detectable signal indicative of the amount of ATP in the sample. Luciferin/luciferase preparations and methods for their use in assaying ATP will be well known to those skilled in the art and are commercially available.

For using a single reagent, ie. ADP and luciferase/luciferin in one reagent, with adenylate kinase testing methods as described herein it is preferred that the reagent DH is adjusted to that which is optimal for both enzymes, ie. a compromise, in order that counting might continue while converting ADP to ATP. This may be determined by routine experiment using known bacterial numbers in a sample.

The sample, ADP and magnesium ion source may be mixed in any buffer providing a pH suitable for the adenylate kinase reaction; no other reagents are necessary. Thus any buffer providing a pH of between 5.5 and 8.5 might be used, with optimal pH lying between pH 6 and 7, preferably pH 6.5. Examples of suitable buffers include Tris and phosphate buffers. Most suitably the sample is collected and/or diluted in such a buffer in preparation for carrying out the method of the invention.

The effect of extractant upon the luciferase/luciferin system is known to be important (see eg. Simpson et al (1991) J. Biolumin Chemilumin 6(2) pp97–106); with cationic detergents being known to potentiate the reaction but to cause gradual inactivation of luciferase, anionic detergent inhibiting the reaction and nonionic and zwitterionic detergents being known to potentiate over a wide range. A mixture of 0.15% cationic detergent together with 0.25% tertiary diamine surfactant (obtained from Celcis, Cambridge, UK) was found to be satisfactory for present purposes, but those skilled in the art will have no problem screening for other 'extractants' that yield an optimal mix of adenylate kinase and luciferase activity when copresent in the same solution.

The light given off from the mixture after all the essential steps are complete, ie. ADP conversion to ATP and subsequent action of luciferase upon luciferin, may be measured by residence of the sample volume, eg. luminometer tube, within a light detector immediately after or simultaneously with addition of the luciferase and luciferin or other agents which enable the essential steps to proceed.

In a second aspect of the present invention there is provided a test kit for performing the method of the invention. The test kit of the present invention comprises the essential reagents required for the method of the invention, ie. adenosine diphosphate together with luciferase and luciferin. Preferably the kit includes all these reagents with the luciferase and luciferin being provided as a single reagent solution, with a further detergent in the kit reagent suitable for disrupting the target cells for which the assay is intended. Usually for assaying microorganisms only cationic detergent is needed, whereas if fungal spores and eucaryotic, eg. somatic, cells ape likely to be significant then a further nonionic detergent reagent might be included to asess their numbers. The kit is in the form of a single package preferably including instructions as to how to perform the method of the invention; the reagents being provided in containers and being of strength suitable for direct use or after dilution. Phosphate buffer may be included.

A preferred test kit of the invention comprises ADP reagent which is of purity higher than 99.95%, and a luciferase reagent that is substantially free of adenylate kinase activity. Alternatively the luciferase/luciferin ratio used, reflected in the kit instructions for use and/of in their relative concentrations, is such that the luciferase is capable of acting upon the luciferin substrate sufficiently quickly such that the luciferase associated adenylate kinase produces ATP after the initial emission is finish; thus microorganism derived adenylate kinase will be indicated by a flash kinetic reaction and contaminant DNA by a glow.

The preferred purified reagents may be provided by the methods described above. It is noted that adenylate kinase activity in luciferase may be deleted by leaving the luciferase to stand fop a period of months or years.

In a still more preferred form of the second aspect of the present invention there is provided a test kit comprising the essential reagents required for the preferred method of the invention, ie. the characterising purified adenosine diphosphate, a source of magnesium ions and preferably luciferase and luciferin. Preferably the kit includes all these reagents, with the luciferase and luciferin being provided as a single reagent solution, with a detergent reagent in the kit suitable for disrupting the target cells for which the assay is intended. Usually for assaying microorganisms only cationic detergent is needed, whereas if fungal spores and somatic cells are likely to be significant then a further nonionic detergent reagent might be included to assess their numbers. The kit is in the form of a single package preferably including instructions as to how to perform the method of the invention; the reagents being provided in containers and being of strength suitable for direct use or after dilution.

It may be appropriate to provide the magnesium ions with the luciferase/luciferin reagent if this is to be added before the ADP to ATP coversion has begun, but then they should be in excess over that bound to the EDTA or phosphate in that reagent and should be optimised to accomodate both adenylate kinase and luciferase requirements. For microbial detection magnesium ions are preferably provided with a sample collection/dilution buffer but other formats may be preferred for particular applications. Most conveniently the magnesium ions are provided with a sample collection or dilution buffer, the ADP is provided with detergent/surfactant extractants and optionally with a stabiliser such as EDTA, and the luciferase and luciferin are provided together, thus providing a three reagent test kit. Alternatively these agents may be provided in the form of a single reagent that is freeze dried such that they do not interact to cause degredation of eg. the ADP, prior to use.

A particularly preferred test kit of the invention comprises ADP reagent which is of purity higher than 99.999%, magnesium ions and a luciferase/luciferin reagent, including BSA, that is substantially free of adenylate kinase activity. Alternatively the luciferase/luciferin ratio used, reflected in the kit instructions for use and/or in their relative concentrations, is such that the luciferase is capable of acting upon the luciferin substrate sufficiently quickly such that any luciferase associated adenylate kinase produces ATP after the initial emission is finished; thus microorganism derived adenylate kinase will be indicated by a flash kinetic reaction and contaminant ATP by a glow.

The preferred purified reagents may be provided by the methods described above. It is noted that adenylate kinase activity in luciferase may also be depleted by leaving the luciferase to stand for a period of months or years.

In a third aspect of the present invention there is provided an apparatus for performing the method of the invention. The apparatus of the present invention is characterised in that it comprises means for receiving a sample to be analysed for the presence of microorganisms as an aqueous suspension thereof, means for addition of ADP, luciferase and luciferin to the suspension and means for detecting light produced. Preferably the apparatus includes a means for adding detergent to the suspension before the means for adding the luciferase and luciferin. Preferably the ADP, and in preferred apparatus magnesium ions, is/are added before the luciferase and luciferin, e.g. with the detergent, to allow time for the generation of ATP, but all agents may be added together if using glow kinetics. Preferably the luciferase/luciferin reagent(s) is/are added separately from the ADP.

Preferably the apparatus includes a detection means for determining the amount of light emitted from the suspension on addition of the luciferase and luciferin and optionally includes a computer processor and visual display unit for receiving a signal for the detection means indicative of the amount of light emitted and for calculating from that the likely presence and amount of microorganisms and displaying results. Such calculation might be facilitated by programing the processor to take account of a set order of incoming signals, some of which will be controls including blank and nonionic detergent runs, or take account of pre-input standards eg. temperature.

A preferred apparatus will include a conveyor means which receives a volume of liquid medium holding the sample from one or more reagent stations to the light detection means. Thus for example a conveyor receives a series of sample vessels, preferably luminometry vessels, which are preloaded with an phosphate including aqueous liquid suspension of material to be tested for the presence of microorganisms or which are passed through a station of the apparatus where such suspension is placed therein. The vessels for example may be open topped and passed thereafter on the conveyor under a detergent adding station, under ADP and luciferase/luciferin adding station and then through a light detector station. The light detector may be of standard luminometer format eg. Biotrace Multi-lite or Biotrace M3.

Light may be measured by residence of the sample volume, eg. luminometer tube, within the light detector immediately after or simultaneously with addition of the luciferase and luciferin. Thus in a preferred apparatus the luminometry reagents are added just prior entry into or within the light detector station. A preferred apparatus measures the light emitted immediately after reagent addition, then again after a set period of time. Alternatively the light emmited is detected over a suitably long period such that it can be assessed cumulatively eg. where glow kinetics are used.

The methods, apparatus, reagents and kits of the present invention will now be illustrated by way of example only with reference to the following non-limiting Examples. Further embodiments of the invention will occur to those skilled in the art in the light of these.

DESCRIPTION OF THE PREFERRED EMBODIMENTS

Figure 1:
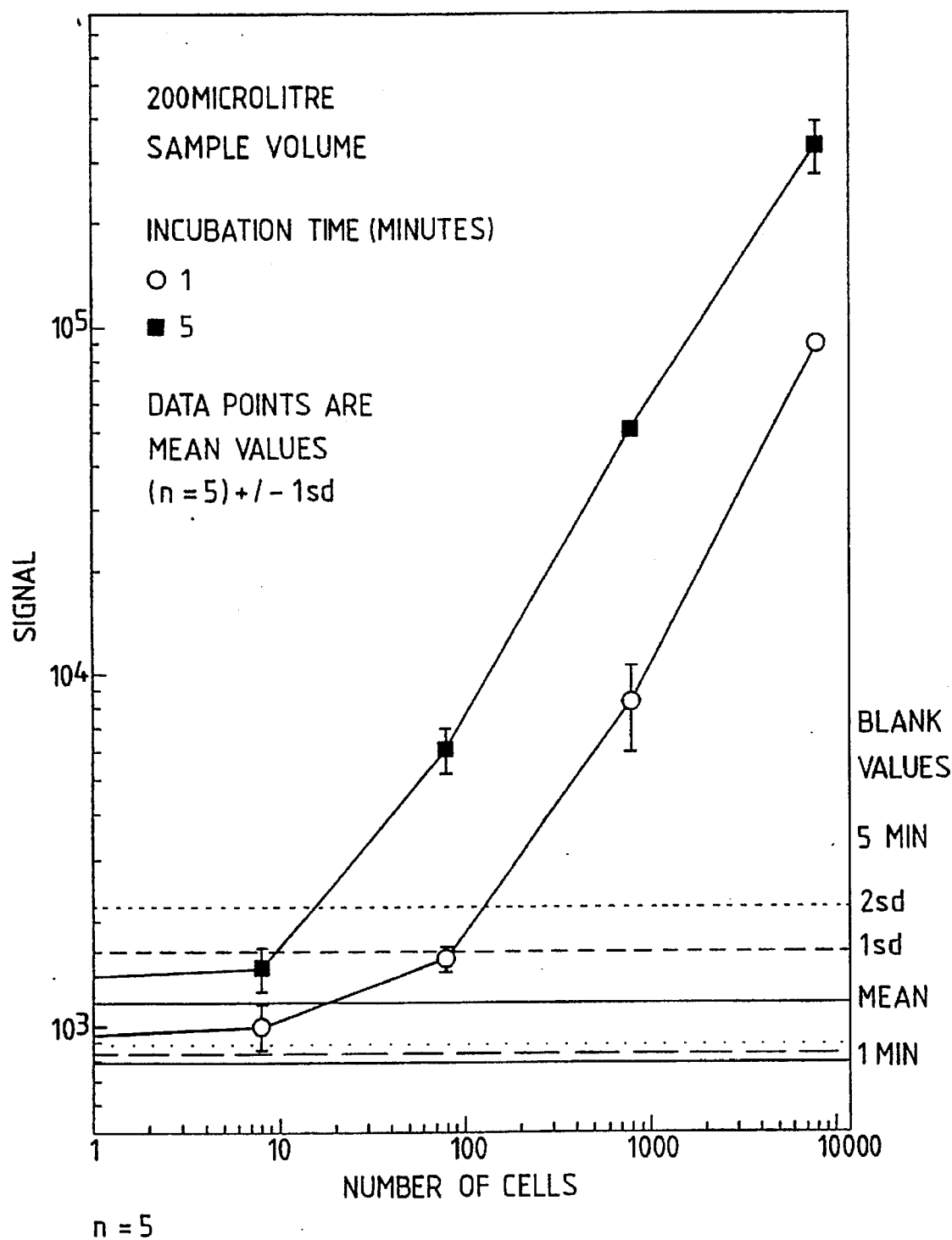

FIG. 1: plots log luminometer signal against log number of *E. coli* in a 200 μl sample using the improved assay Example 14 using 1 and 5 minute incubations prior to luciferin/luciferase addition.

Figure 2:
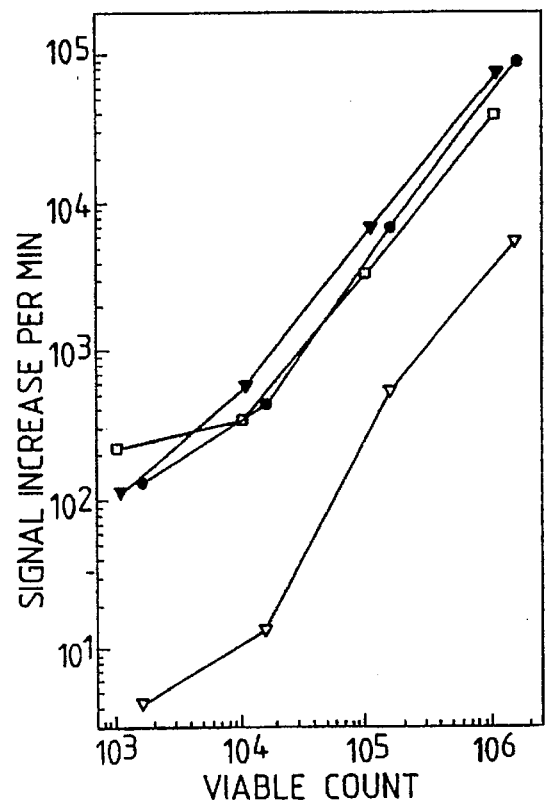

FIG. 2: shows a graph of increase in luminometer counts per minute for various amounts of *E. coli* assayed according to Examples 4 and 5.

Figure 3:
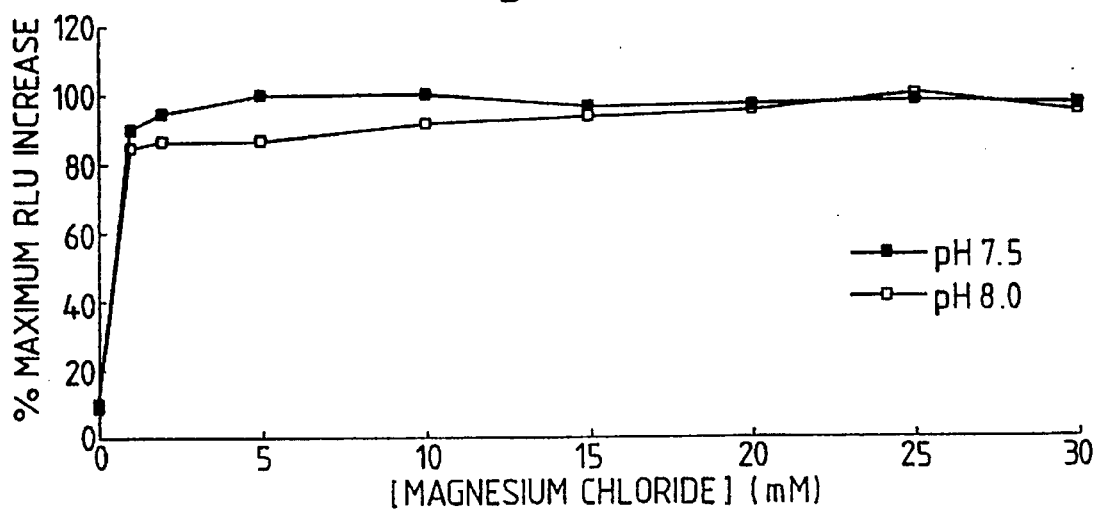

FIG. 3: shows the effect of magnesium ion concentration upon the luminometer signal derived from a set number of *P. aeruginosa* at pH 7.5 and pH 8.0 showing the 10 fold increase over no added magnesium.

Figure 4:
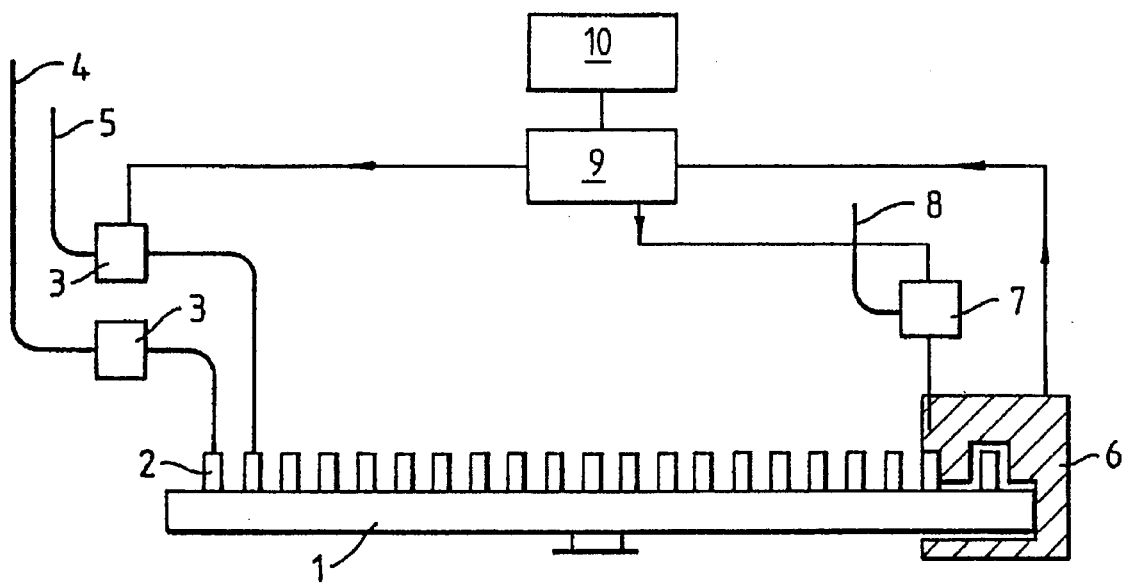

FIG. 4: shows a diagrammatic representation of the apparatus of Example 6.

EXAMPLES

EXAMPLE 1

Preparation of purified adenosine diphosphate reagent

Liquid chromatography was used to further purify commercial high purity (>99.95%) ADP (Sigma). Small columns were made from 10 ml disposable plastic syringe bodies and circles of glass fibre filter paper (Whatman GF/A) were placed inside the columns covering their outlets. The chromatographic medium, diethylaminoethylcellulose (Whatman DE-52), was carefully poured into each column and allowed to settle, giving a bed volume of about 4 mls. Another glass filter paper circle was placed on top of the column packing.

After washing the column with about 15 mls of eluent (0.02M HCl), 100 mM high purity ADP in about 0.5 mls of 0.02M HCl was applied and elution carried out with 0.02M HCl flowing at 1 ml per minute. Fractions of 3 to 4 mls were collected in disposable plastic cuvettes which allowed the optical density—and thereby the ADP—to be monitored conveniently (at 265 nm). The initial fractions, with high ADP:ATP ratios, were retained for use.

To determine the success of this purification, commercially available luciferin/luciferase preparations (Enzymatrix, Cambridge, UK and HM by Biotrace, Bridgend, UK) were used according to the manufacturers instructions to detect the amount of ATP present. Similar tests were carried out in the presence of adenylate kinase to determine ADP levels.

50 μl of a 1/3,000 dilution of 100 mM commercial (Sigma) high purity ADP gave a luminometer count of 8,919, this being a measure of ATP impurity levels. After incubation with 100 femtomoles of adenylate kinase the same sample gave a count of 1,370,839, this being a measure of the quantity of ADP. A column purified fraction derived from this ADP solution gave an ATP count of 223 and an adenylate kinase count of 1,442,054 under the same conditions. The signal to background ratio in this case was improved from 153 to 6466.

EXAMPLE 2

Alternative preparation of adenosine diphosphate reagent

High purity ADP was further purified by the action of apyrase on contaminating ATP. 0.1 mM solutions were made with ADP derived from two different sources. One (A) was sold as 98% pure and the other (B) as 99% pure. Commercially available luciferin/luciferase preparations were used to determine ATP, the luminometer counts from samples A and B being 54,768 and 305,500 respectively. 8 μls of a 100 unit per ml solution of apyrase (potato apyrase: Sigma) were then added to 10 mls of 0.1 mM solutions of A and B. After incubation at room temperature for about 22 hours followed by boiling to destroy the apyrase, luminometer counts of 5,100 for A and 6,600 for B were obtained showing a marked decrease in the amount of contaminating ATP.

EXAMPLE 3

Assessment of assay of free adenylate kinase

Stock solutions of the adenylate kinase for assay were made in pH 7.2 phosphate buffered saline containing 1% BSA and 0.25% Triton X-100. and the assay was performed in disposable 3 ml plastic tubes suitable for luminometry. 200 μl of pH 7.8 Tris buffer was pipetted into the assay tube and to this was added 100 μl of approximately 1 mM ADP (purified as detailed above). 10 μl of adenylate kinase, diluted in pH 7.8 Tris buffer, was then added to start the reaction. The tube was whirli-mixed and left to incubate at room temperature. After incubation for 10 minutes, 100 to 150 μl of luciferin/luciferase reagent was added and the light output from the ATP formed by activity of the adenylate kinase was measured immediately in a luminometer (see Table 1).

It should be noted that the sensitivity of the assay can be increased by using higher concentrations of ADP in the reaction medium as the $K_m$ for adenylate kinase is in the millimolar range. Commercially available ADP containing significant amounts of ATP, renders use of such millimolar quantities of ADP undesirable but use of the purified ADP of the invention allows such increase with attendant advantages. Increasing time of incubation likewise will increase sensitivity.

TABLE 1 relationship between the amount of ATP detected and the amount of adenylate kinase (AK) present: amplification is ATP formed/mole AK in 10 minute incubation.

| Moles of AK | pMoles of ATP formed | Amplification |
|---|---|---|
| 1 femtomole | 322 | 320000 |
| 500 attomoles | 235 | 470000 |
| 250 attomoles | 97.5 | 390000 |
| 125 attomoles | 55.2 | 440000 |
| 62 attomoles | 26.5 | 420000 |
| 31 attomoles | 12.7 | 400000 |
| 16 attomoles | 5.7 | 360000 |
| 8 attomoles | 3.9 | 500000 |
| 4 attomoles | 2.1 | 540000 |
| 2 attomoles | 0.8 | 410000 |
| 1 attomole | 0.6 | 610000 |
| 0.5 attomole | 0.3 | 610000 |

Unknown adenylate kinase levels were estimated by reference to a calibration curve relating known concentrations of adenylate kinase to ATP produced in the 10 minute incubation. Because of the sensitivity of the assay it is desirable to take precautions against accidental contamination by ATP of adenylate kinase. Assays should be carried out in a laminar flow hood using ATP free solutions disposable rubber gloves and low ATP-plastics consumables where possible.

It will be realised that when adenylate kinase is being used to determine the likely presence of particular organisms accurate quantification may be enhanced if the amount of adenylate kinase they are expected to contain is be estimated. Hence calibration curves made up using the specific target organisms might be best used.

EXAMPLE 4

Assay of *E. coli*

A one week old *E. coli* broth culture containing approximately $2.2 \times 10^7$ microorganisms per 200 μl of phosphate buffered saline pH 7.4 was used as stock and diluted in successive dilutions of 10 with that buffer to give a range of samples of from $10^7$ to 0.1 organisms per 200 μl sample. The buffer provides phosphate reactant for ATP synthesis.

Each 200 μl sample was added to a 3 ml luminometer tube, 10 μl 1 mM ADP and 100μl of 0.1% aqueous cetyl trimethyl ammonium bromide added and the resultant mixture incubated at room temperature for 1 minute. On completion of the incubation 100 μl aged Blotrace HM (2 years old having no detectable adenylate kinase activity) was added and the light emitted determined over a first 10 second interval and then over 10 second intervals up to one minute to determine the increase in light in cumulative fashion using a Blotrace M3 luminometer. The initial signal value was subtracted from the final reading to gain a measure of the signal in counts per minute.

Counts above control obtained over the minute incubation varied with number of *E. coli* as follows: $10^6$–39297 cpm; $10^5$–3199 cpm; $10^4$–189 cpm; $10^3$–67 cpm; $10^2$–26 cpm. Further results are shown in FIG. 1.

The effect of extractant upon the luciferase/luciferin system is known to be important (see eg. Simpson et al (1991)

J. Biolumin Chemilumin 6(2) pp97–106); with cationic detergents being known to potentiate the reaction but to cause gradual inactivation of luciferase, anionic detergent inhibiting the reaction and nonionic and zwitterionic detergents being known to potentiate over a wide range, In order to assess the effects of detergent upon the adenylate kinase assay of E. coli cells the protocol used above was altered in so far as different 'extractants' were used to assay $10^7$ E. coli in 200 μl of phosphate buffered saline.

The highest counts were obtained using Lumac NRM (241927 cpm) and CETAB (226924 cpm) while two other extractants gave 79,280 and 29,280 cpm respectively. This is not surprising in the light of the Simpson et al. findings regarding the deleterious effects of cationic and anionic detergents on luciferase; it being considered likely that these reagents, designed for use with luciferase/luciferin alone for ATP assay, have inhibitory effect on adenylate kinase.

EXAMPLE 5

Location of adenylate kinase detected in E.coli assay

In order to determine the location of the adenylate kinase detected in the assay of Example 4 the number of counts per minute obtained using fresh unwashed E. Coli cells, fresh washed cells, cells stored for 3 days at 37° C. and unwashed and the medium from fresh cells as the sample. The results from these assays showed that most of the adenylate kinase is intracellular, less than 10% being released into the medium, and that the adenylate kinase levels do not vary significantly with the age of the cells. (see FIG. 1)

EXAMPLE 6

Apparatus of the invention

An apparatus of the invention consists of a carousel conveyor (1) mounting racks suitable for holding open topped luminometer tubes (2) with a number of reagent addition stations being placed at various points along its direction of travel. Luminometer tubes (2) containing samples to be assayed are loaded onto the carousel at the start of the run and pass to a first station where computer controlled peristaltic pumps (3) operate a supply of cationic detergent (4) and ADP reagent (5) to deliver the required 100 μl and 10 μl respectively. The carousel run next carries the tube to a luminometer enclosure (6) where simultaneously 100 μl luciferase/luciferin reagent (eg. Biotrace HM) is added using a computer controlled peristaltic pump (7) to control delivery from supply (8). The tube takes at least 1 minute to travel from the detergent/ADP station to the luminometer/luciferase/luciferin station to allow microorganism disruption and ATP synthesis.

After addition of the luciferase/luciferin reagent the tube remains in the luminometer enclosure for 70 seconds while 7 readings of counts/10 second period are taken, with the cumulative value after 10 seconds being subtracted from that after 70 seconds to give the counts per minute. This calculation is carried out in an associated computer (9) fed with a cpm signal by the luminometer and results for each tube applied to the carousel displayed on a visual display unit (10). In this fashion the computer is capable of controlling the time of delivery of reagents to a known tube to vary the incubation period if required.

EXAMPLE 7

Test kit of the invention

A test kit of the invention consists of a container holding purified ADP solution (>99.95% pure) prepared as described in Example 1 or 2 at 10 mM (increased concentration to that of the method described in Example 4 to increase sensitivity); a container holding aged luciferase/luciferin solution (Blotrace HM) and a container holding cetyl trimethyl ammonium bromide (0.1% in water); all packaged together with instructions as to use in the method of the invention. For use in mobile laboratories the package may be in the form of a plastics box having resilient mountings for each container, ie foam filling with recesses in the shape of the container exterior.

Optionally included in the package is a container of nonionic detergent solution (Triton X-100 0.2% or equivalent) and/or a container holding an ATPase such as apyrase for the destruction of ATP released by the action of the nonionic detergent on a sample rendering it suitable for reassay by addition of the cationic detergent.

Phosphate buffer may be included in the kit as a separate buffer or may be included in the detergent or ADP reagent containers particularly if these are in final concentration. Alternatively the buffer may be included with the detergent and/or ADP in a concentrated form for dilution.

EXAMPLE 8

Preparation of adenosine diphosphate reagent of greater than 99.999% purity with respect to ATP, Liquid chromatography was used to further purify commercial high purity (>99.95%) ADP (Sigma) using a 5 ml Econopac Q cartridge (Biorad) equilibrated with 20 mM potassium phosphate pH 4.6 and loaded with 5 ml of the 1 mM ADP (2.1 mg). Elution was carried out by steps of $KP_i$ concentration up to 400 mM whereupon the ADP was strongly retained and eluted as a peak at approximately 340 mM $KP_i$. Setting the system up with a pump (5 ml/min) and gradient mixer, a gradient of 50 to 1M $KP_i$ in 200 ml total was provided and 5 ml fractions collected. ADP eluted as a sharp peak between fractions 12 and 17 with ATP beginning to appear at the end of the gradient. A step in $[KP_i]$ to 1M eluted the remaining ATP. The purest ADP fractions from this column were of less than $2\times10^{-8}$ mole % ATP.

EXAMPLE 9

Preparation of adenylate kinase free luciferase reagents

Adenylate kinase activity was deleted from commercially available luciferin/luciferase reagents (Blotrace HM) by ageing, including several months at high ambient temperature (circa 30° C.) over a period of 12 months in dry form.

EXAMPLE 10

Alternative preparation of kinase free luciferase reagents

Commercially available luciferase is purified using column chromatography by the method of Devine et al (1993) using Blue Sepharose as referred to above.

EXAMPLE 11

Preparation of adenylate kinase Free BSA

Sigma Fraction V (RIA Grade, Cat. No. A-7888) BSA was made up at 1% weight/volume in 200 ml sterile water to give a starting pH of 5.6. Two 50 ml samples of this were put into 100 ml Duran bottles, the remainder made to pH 10 using 5M NaOH and 50 ml put into each of two Durans. Thimerosal was added to 0.02% final concentration as a preservative to prevent microbial growth and the bottles incubated at 37° C. or 50° C. for 24 hours before the pH of each was readjusted to 7.6 with 5M HCl or 5M NaOH as appropriate.

Adenylate kinase activity was measured by mixing 100 μl BSA sample as prepared above with 100 μl 30 mM magnesium acetate solution, placing the resultant mixture in a 3.5 ml luminometer tube in a luminometer and adding 100 μl ADP solution prepared in Example 1 and 100 μl luciferin/ luciferase reagent (Celcis, Cambridge UK) that was prepared free of adenylate kinase activity by use of column chromatography and chemically treated BSA.

After a 5 second delay light emission integrated over 10 seconds was measured and recorded on a computer and a total of 10 sequential 10 second readings were made to determine the rate of ATP production; analyses being performed in duplicate. Calibration was made using 4 replicate measurements of the light emitted from 5 μl of 10 ng/ml (91 femtomoles) of ATP in water: mean signal 2950 per femtomole.

Results: The BSA sample incubated at 37° C. remained clear whilst those at 50° C. formed a precipitate which was slight at pH 10 and very heavy at pH 5.6. At pH 10 and 50° C. there was slight discolouration. Adenylate kinase activity remaining in these samples is shown below in Table 2 below as represented by luminometer counts pep minute.

It is recommended that still milder forms of inactivation are used, with longer duration, or that the BSA is immediately freeze dried, if it is intended to store it for any length of time as after 2 weeks even the pH 10 50° C. sample became unuseable due to increased discolouration. The 37° C. samples did not go off in this manner and thus offer better scope for reducing stable adenylate kinase free BSA by increasing the incubation time. The fact that the Biotrace HM agent lost its activity in dry form after storage at 40° C. demonstrates the possibilities here.

TABLE 2

| Treatment | Counts t5–15 | Counts t95–105 | Difference | d[ATP]/dt (fm · sec$^{-1}$) |
|---|---|---|---|---|
| 37/5.6 | 9350 | 41727 | 23207 | 7.1 |
|  | 9845 | 26041 | (means) |  |
|  | 11896 | 32945 |  |  |
| 37/10 | 7192 | 30602 | 17943 | 5.5 |
|  | 5047 | 20557 |  |  |
|  | 4469 | 19377 |  |  |
| 50/5.6 | 606 | 1191 | 595 | 0.18 |
|  | 343 | 948 |  |  |
| 50/10 | 460 | 1014 | 500 | 0.15 |
|  | 342 | 847 |  |  |
|  | 314 | 754 |  |  |

EXAMPLE 12

Preparation of luciferin/luciferase reagent with adenylate kinase free BSA

Commercial preparations of luciferin/luciferase commonly contain BSA as necessary. BSA chemically treated as set out in Example 11 above or as commercially available as acetylated BSA (e.g. BDH or Sigma) was admixed with adenylate kinase free luciferase in normal proportions together with other standard Celcis agents such as to provide a Celcis LDR luciferin/luciferase luminescence reagent of adenylate kinase activity less than $10^{-9}$ U assay volume (ie. 300 μl).

EXAMPLE 13

Test kit of the invention

A test kit of the invention is provided consisting of the following:

(i) a container holding 15 mM magnesium acetate solution for collection/dilution of samples;

(ii) a container holding purified ADP solution (>99.99999998% pure with regard to ATP) prepared as described in Example 8 in a concentration of 0.3 mM in potassium phosphate (7.5 mM pH 6.5) buffer solution further including 0.2 mM EDTA and a mixed extractant of 0.15% cationic detergent and 0.25% tertiary diamine surfactant.

(iii) a container holding luciferin/luciferase LDR (Celcis, Cambridge, UK) bioluminescence reagent of adenylate kinase activity less than $10^{-8}$ U/100 μl.

Optionally included in the package is a container of nonionic detergent solution (Triton X-100 0.2% or equivalent) and/or a container holding an ATPase such as apyrase For the destruction of ATP released by the action of the nonionic detergent on a sample rendering it suitable For teassay by addition of the cationic detergent.

EXAMPLE 14

Assay of known amounts of E. coli using method of the invention and kit of Example 13

A one week old E. coli broth culture containing approximately $2.2 \times 10^7$ microorganisms per 200 μl of phosphate buffered saline pH 7.4 was used as stock and diluted in successive dilutions of 10 with the collection/dilution reagent containing magnesium ions ((i) in Example 6) to give a range of samples of from $10^7$ to 0.1 microorganisms per 200 μl sample.

Each 200 μl sample was added to a 3.5 ml luminometer tube, 100 μl of ADP/extractant reagent ((ii) in Example 13) added and the mixture, total volume 300 μl, was incubated at room temperature for 1 or 5 minutes. On completion of the incubation 100 μl of modified Celcis LDR bioluminescence reagent, ((iii in Example 13 above) was added and the light emitted determined over a first 10 second interval and then over 10 second intervals up to one minute to determine the increase in light in cumulative fashion using a Biotrace M3 luminometer. The initial signal value was subtracted from the final reading to gain a measure of the signal in counts per minute.

The efficacy of the present method can be seen by reference to FIG. 3 where statistically valid linear response between number of E. coli and light emitted by the sample mix after 5 minute incubation with ADP is obtained for 10 organisms per sample and upward, for 100 organisms and upward with a 1 minute incubation, and a detection limit of about 10 organisms is given in both cases. This compares very favourably with the method where magnesium ions are not included and using less pure ADP, luciferase and BSA which gives a difference of only 26 cpm after a 1 minute incubation with 100 organisms and 67 cpm with 1000; linear responses only being obtained with 1000 cells and over. By comparison 1000 cells per sample in the present method gives a signal increase of several thousand cpm after 1 minute.

It will be realised that in order to perform an assay for an unknown number of microorganisms in a sample using the present method, a calibration curve may be provided plotting known numbers of microorganisms against luminometer counts as shown in the FIGS. 3 and 4 (eg. as log values), deriving a number of counts from a sample containing the unknown number of microorganisms (including zero organisms) using the same protocol, and estimating the number of microorganisms in the sample as being that corresponding to the same number of counts on the curve.

It will be realised by those skilled in the art that the amount of adenylate kinase present in a particular microorganisms, eg. bacteria, may vary from other microorganisms. For example, yeasts contain more adenylate kinase than bacteria by virtue of their size, and indeed single yeasts can be detected by this method. Thus for a given microorganism a particular calibration curve may be required, and it may be necessary to provide such curves for different states of the same microorganism, eg. for weakened, pH or oxygen stressed organisms. However, a further advantage of the present method over existing ATP based methodology is that adenylate kinase content will be more closely correlated to cell numbers than the highly variable ATP content which is depleted by cell metabolism.

I claim:

1. A method for determining the presence and/or amount of microorganisms and/of their intracellular material present in a sample wherein the amount of adenylate kinase in the sample is estimated by mixing the sample with adenosine diphosphate (ADP), determining the amount of adenosine triphosphate (ATP) produced by the sample from this ADP, and relating the amount of ATP so produced to the presence/or amount of microorganisms and/or their intracellular material.

2. The method as claimed in claim 1 wherein conversion of ADP to ATP is carried out in the presence of magnesium ions at a molar concentration sufficient to allow maximal conversion of ADP to ATP.

3. The method as claimed in claim 1 wherein sufficient magnesium ions are present to provide one mole of magnesium for one mole of ADP such that all of the ADP molecules may be associated with at least one magnesium ion.

4. The method as claimed in claim 1 wherein the sample is provided in the form of an aqueous suspension or solution and the estimation of microorganisms and/or intracellular material therein is carried out by adding ADP and magnesium ions to the sample under conditions whereby any adenylate kinase present will convert ADP to ATP, incubating the sample for a predetermined period to effect such conversion, adding luciferase and luciferin agents, determining the amount of light emitted from the sample and relating that to presence and amount of microorganisms and/or intracellular material.

5. The method as claimed in claim 1 wherein the amount of ADP with which the sample is mixed is sufficient to provide an ADP concentration in the mixture in excess of 0.005 mM.

6. The method as claimed in claim 5 wherein the ADP is in excess of 0.08 mM.

7. The method as claimed in claim 5 wherein the ADP concentration is about 0.1 mM.

8. The method as claimed in claim 2 wherein the concentration of magnesium ions in the suspension or solution during conversion of ADP to ATP is 1 mM or more.

9. The method as claimed in claim 2 wherein the concentration of magnesium ions in the suspension or solution is 10 mM or more.

10. The method as claimed in claim 2 wherein the magnesium ions are provided in the form of magnesium acetate.

11. The method as claimed in claim 1 wherein the luciferin/luciferase luminescence reagents are added to the sample at the beginning of the incubation as a single reagent with the ADP and magnesium ion source.

12. The method as claimed in claim 2 wherein the magnesium ion source and the ADP are kept in dry form or in separate solutions prior to use and brought together or made into an aqueous solution immediately prior to use or in the ADP conversion step.

13. The method as claimed in claim 2 wherein the magnesium ion source and sample are mixed together before adding the ADP.

14. The method as claimed in claim 13 wherein the sample is collected or diluted in a solution comprising the magnesium ion source.

15. The method as claimed in claim 1 wherein the conversion of ADP to ATP is carried out at a pH of between 5.5 and 8.5.

16. The method as claimed in claim 1 wherein the ADP has a molar % ATP of less than 0.001%.

17. The method as claimed in claim 1 wherein the ADP has a molar % ATP of $2 \times 10^{-8}$ or less.

18. The method as claimed in claim 1 wherein the ADP is stored prior to use in the presence of a chelating agent to prevent contaminant adenylate kinase converting it to ATP prematurely.

19. The method as claimed in claim 4 wherein the luciferase/luciferin reagent has an adenylate kinase content of less than $10^{-7}$ U/ml.

20. The method as claimed in claim 19 wherein the luciferase/luciferin reagent comprises bovine serum albumin that has been chemically treated to deplete its adenylate kinase activity.

21. The method as claimed in claim 1 wherein the sample is treated with an extractant which disrupts microorganism cells and exposes their adenylate kinase to the ADP and magnesium ions.

22. The method as claimed in claim 21 wherein the cells are fungal spores or eucaryotic cells and the extractant comprises a non-ionic detergent.

23. The method as claimed in claim 21 wherein all cells are to be detected and/or quantified and the extractant comprises a cationic detergent.

24. The method as claimed in claim 21, wherein the extractant further comprises a surfactant.

25. The method as claimed in claim 21, wherein the cells are bacterial cells wherein the ATP released by non-ionic detergent is subtracted from the ATP released by cationic detergent and surfactant, and the remainder related to bacterial cell numbers.

26. A test kit for detection and/or quantification of microorganisms and/or the cellular material comprising one or more reagents including a reagent comprising ADP with a molar % ATP of less than 0.001.

27. A test kit as claimed in claim 26 further comprising a source of magnesium ions.

28. A test kit as claimed in claim 26 further comprising an extractant suitable for exposing adenylate kinase present in microorganisms to ADP in solution therewith such that conversion of the ADP to ATP takes place.

29. A test kit as claimed in claim 26 further comprising luciferase and luciferin in the form of a bioluminescence reagent capable of emitting light in the presence of ATP.

30. A test kit as claimed in claim 27 wherein the source of magnesium ions is provided as a sample collection or dilution buffer solution.

31. A test kit as claimed in claim 30 wherein the collection or dilution buffer solution comprises magnesium acetate.

32. A test kit as claimed in claim 26 wherein the ADP is in a reagent together with a detergent and/or surfactant extractant.

33. A test kit as claimed in claim 26 wherein the ADP, a magnesium ion source and a bioluminescence reagent are provided in three separate containers.

34. A test kit as claimed in claim 26 wherein the reagents are all provided as single freeze dried reagents.

35. A test kit as claimed in claims 26 wherein the ADP is of purity of 99.99999998% or more with respect to ATP.

36. A test kit as claimed in 29 comprising a bioluminescence reagent of adenylate kinase activity less than $10^{-7}$ U/ml as defined herein.

37. A test kit as claimed in claim 29 wherein the bioluminescence reagent comprises bovine serum albumin that has been chemically treated to deplete its adenylate kinase activity.

38. A test kit as claimed in claim 26 wherein the ADP reagent further comprises a chelating agent in sufficient amount to prevent contaminating adenylate kinase from converting ADP to ATP.

39. An apparatus comprising a means for receiving a sample to be analysed for the presence of microorganisms or their intracellular contents in an aqueous suspension or solution, means for addition of ADP, luciferase and luciferin to the suspension and means for detecting light produced wherein a conveyor is provided for moving the sample and means relative to each other for the purpose of sequential operation.

40. An apparatus as claimed in claim 39 further comprising a means for adding a source of magnesium ions to the sample prior to the means for detecting light produced.

41. An apparatus as claimed in claim 39 further including a means for adding detergent to the suspension before the means for adding the luciferase and luciferin.

42. An apparatus as claimed in claim 41 wherein the ADP reagent is added with the detergent.

43. An apparatus as claimed in claim 39 further including a light detecting station where luciferase and luciferin are added to the sample prior to monitoring light emitted therefrom with the means for detecting light.

44. An apparatus as claimed in claims 39 comprising a conveyor means which receives a volume of liquid medium holding the sample and carries it through one or more reagent stations to the light detection means.

45. An apparatus as claimed in claim 39 comprising a conveyor adapted to receive a series of luminometry vessels which are preloaded with an aqueous liquid suspension of material to be tested for the presence of microorganisms or which are passed through a station of the apparatus where such suspension is placed therein.

* * * * *